United States Patent
Timken et al.

(10) Patent No.: US 11,000,839 B2
(45) Date of Patent: *May 11, 2021

(54) REGENERATION OF AN IONIC LIQUID CATALYST BY HYDROGENATION USING A MACROPOROUS NOBLE METAL CATALYST

(71) Applicant: Chevron U.S.A. Inc., San Ramon, CA (US)

(72) Inventors: Hye Kyung Cho Timken, Albany, CA (US); Jeff Johns, Draper, UT (US); Rahul Shankar Bhaduri, Moraga, CA (US); Viorel Duma, Hercules, CA (US); John V. Heyse, Crockett, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 629 days.

This patent is subject to a terminal disclaimer.

(21) Appl. No.: 15/866,588

(22) Filed: Jan. 10, 2018

(65) Prior Publication Data

US 2018/0353945 A1 Dec. 13, 2018

Related U.S. Application Data

(62) Division of application No. 15/194,979, filed on Jun. 28, 2016, now Pat. No. 9,956,553.

(51) Int. Cl.
*B01J 31/02* (2006.01)
*B01J 31/40* (2006.01)
(Continued)

(52) U.S. Cl.
CPC ...... *B01J 31/0277* (2013.01); *B01D 15/1871* (2013.01); *B01J 20/103* (2013.01);
(Continued)

(58) Field of Classification Search
CPC ....... C07C 2/58; C07C 9/16; C07C 2527/125; C07C 2531/02; B01D 15/1871;
(Continued)

(56) References Cited

U.S. PATENT DOCUMENTS

| | | | |
|---|---|---|---|
| 4,642,179 A | 2/1987 | Morales et al. | |
| 5,217,603 A | * 6/1993 | Inoue | B01J 35/1038 208/251 H |

(Continued)

FOREIGN PATENT DOCUMENTS

| | | |
|---|---|---|
| CN | 1335368 A | 2/2002 |
| WO | 2007136340 A1 | 11/2007 |

OTHER PUBLICATIONS

PCT International Search Report, International Application PCT/US2017/016795 dated May 8, 2017, pp. 1-5.

*Primary Examiner* — Anthony J Zimmer
*Assistant Examiner* — Syed T Iqbal
(74) *Attorney, Agent, or Firm* — E. Joseph Gess; Melissa M. Hayworth; Terrence M. Flaherty

(57) ABSTRACT

Provided is a hydro-regeneration catalyst system, comprising:
(a) a first graded bed comprising a guard bed material; and
(b) a second graded bed, fluidly connected to the first graded bed, comprising a noble metal catalyst on a support having mesopores and macropores; wherein the noble metal catalyst has an average pore diameter of 20 to 1,000 nm (0.02 to 1 μm), a total pore volume of greater than 0.80 cc/g, and a macropore volume of 0.10 to 0.50 cc/g. Also provided is a guard bed system, comprising:
(a) a first guard bed comprising a first adsorbent having 10 μm or larger pores with an average pore diameter of 100 to 1,000 μm; and
(Continued)

(b) a second guard bed fluidly connected to the first guard bed, comprising a second adsorbent material having mesopores and macropores with a second average pore diameter of 20 to 1,000 nm.

19 Claims, 7 Drawing Sheets

(51) Int. Cl.
| | |
|---|---|
| *B01D 15/18* | (2006.01) |
| *B01J 23/44* | (2006.01) |
| *B01J 38/48* | (2006.01) |
| *C07C 2/58* | (2006.01) |
| *B01J 38/10* | (2006.01) |
| *B01J 23/42* | (2006.01) |
| *B01J 35/10* | (2006.01) |
| *B01J 21/04* | (2006.01) |
| *B01J 20/10* | (2006.01) |
| *B01J 20/16* | (2006.01) |
| *B01J 20/28* | (2006.01) |
| *B01J 23/83* | (2006.01) |
| *B01J 38/08* | (2006.01) |
| *B01J 27/125* | (2006.01) |
| *B01J 31/26* | (2006.01) |

(52) U.S. Cl.
CPC ......... *B01J 20/16* (2013.01); *B01J 20/28083* (2013.01); *B01J 20/28085* (2013.01); *B01J 21/04* (2013.01); *B01J 23/42* (2013.01); *B01J 23/44* (2013.01); *B01J 23/83* (2013.01); *B01J 31/40* (2013.01); *B01J 31/4015* (2013.01); *B01J 35/1047* (2013.01); *B01J 35/1066* (2013.01); *B01J 35/1071* (2013.01); *B01J 38/08* (2013.01); *B01J 38/10* (2013.01); *B01J 38/48* (2013.01); *C07C 2/58* (2013.01); *B01D 2253/104* (2013.01); *B01D 2253/106* (2013.01); *B01D 2253/308* (2013.01); *B01J 27/125* (2013.01); *B01J 31/0231* (2013.01); *B01J 31/0284* (2013.01); *B01J 31/26* (2013.01); *B01J 2231/32* (2013.01); *B01J 2231/323* (2013.01); *B01J 2231/641* (2013.01); *C07C 2527/125* (2013.01); *C07C 2531/02* (2013.01)

(58) Field of Classification Search
CPC ........ B01D 2253/104; B01D 2253/106; B01D 2253/308; B01J 20/103; B01J 20/16; B01J 20/28083; B01J 20/28085; B01J 21/04; B01J 2231/32; B01J 2231/323; B01J 2231/641; B01J 23/42; B01J 23/44; B01J 23/83; B01J 27/125; B01J 31/0231; B01J 31/0277; B01J 31/0284; B01J 31/26; B01J 31/40; B01J 31/4015; B01J 35/1047; B01J 35/1066; B01J 35/1071; B01J 38/08; B01J 38/10; B01J 38/48
See application file for complete search history.

(56) References Cited

U.S. PATENT DOCUMENTS

| | | | |
|---|---|---|---|
| 5,545,602 | A | 8/1996 | Nelson et al. |
| 5,620,592 | A | 4/1997 | Threlkel |
| 5,827,421 | A | 10/1998 | Sherwood, Jr. |
| 5,928,499 | A | 7/1999 | Sherwood, Jr. |
| 5,968,348 | A | 10/1999 | Sherwood, Jr. |
| 6,247,924 | B1 | 6/2001 | Rühl et al. |
| 6,303,531 | B1 | 10/2001 | Lussier et al. |
| 6,388,149 | B2 | 5/2002 | Rühl et al. |
| 6,403,526 | B1 | 6/2002 | Lussier et al. |
| 7,361,714 | B2 | 4/2008 | Grass et al. |
| 8,216,960 | B2 | 7/2012 | Orsenigo et al. |
| 8,772,196 | B2 | 7/2014 | Ackerman et al. |
| 8,795,513 | B2 | 8/2014 | Inamura et al. |
| 8,993,474 | B2 | 3/2015 | Choi et al. |
| 9,956,553 | B2 * | 5/2018 | Timken ................ C07C 2/58 |
| 2002/0013216 | A1 | 1/2002 | Broekhoven et al. |
| 2003/0181779 | A1* | 9/2003 | Broekhoven ............ B01J 35/10 585/709 |
| 2007/0017850 | A1* | 1/2007 | Euzen ................ B01J 23/883 208/58 |
| 2008/0017036 | A1* | 1/2008 | Schultink .............. B01J 20/321 96/135 |
| 2015/0266004 | A1* | 9/2015 | Kumatani ............ B01J 35/1014 502/304 |

* cited by examiner

REGENERATION OF AN IONIC LIQUID CATALYST BY HYDROGENATION USING A MACROPOROUS NOBLE METAL CATALYST

This application is a divisional of U.S. application Ser. No. 15/194,979, titled: "REGENERATION OF AN IONIC LIQUID CATALYST BY HYDROGENATION USING A MACROPOROUS NOBLE METAL CATALYST", filed on Jun. 28, 2016, in Group Art Unit 1736, and published as US20170368544A1, herein incorporated in its entirety.

TECHNICAL FIELD

The present disclosure is directed to macroporous noble metal catalysts and processes for using such catalysts in regenerating deactivated ionic liquid catalyst containing conjunct polymer.

BACKGROUND

Acidic ionic liquids are attractive as catalysts in many refinery and petrochemical process applications where the ionic liquid catalyst is easily mixed with the reactants in a reactor, followed by separation of the catalyst and hydrocarbon product in a settler. Ionic liquid catalysts are particularly useful for hydrocarbon conversion processes such as alkylation, olefin oligomerization, isomerization and disproportionation.

Conjunct polymers are by-products of the hydrocarbon reaction using ionic liquids, and they form a complex with the Lewis acid portion of the ionic liquid catalyst. The ionic liquid catalyst loses its effectiveness over time as the amount of conjunct polymer increases. The ionic liquid catalyst must then either be replaced or regenerated. Because ionic liquids are typically fairly expensive, processes for regenerating the ionic liquid catalysts are needed.

Ionic liquid catalyst can be regenerated by reacting with hydrogen gas in the presence of a solid hydrogenation catalyst under hydrogenation conditions ("hydro-regeneration"). Under hydro-regeneration process conditions, the conjunct polymers are liberated from the ionic liquid catalyst and cracked down to lighter molecules which are extracted downstream by solvent extraction and the regenerated ionic liquid catalyst recovers its activity.

Over the course of the hydro-regeneration process, the regeneration reactor occasionally suffers from pressure build-up primarily due to the formation of by-products that may ultimately result in undesirable process shut-down. Unwanted by-products may include corrosion product metals, gummy oligomers, cokes, and hydrolyzed solids formed as a consequence of trace water or polar hydrocarbons in the feed. It is believed that the pressure build-up is due to localized accumulation of these by-products on the external surface of the solid hydrogenation catalyst bed; this in turn creates higher flow resistance to the ionic liquid catalyst. Localized plugging of the solid hydrogenation catalyst may result in early termination of the regeneration process and a shortened catalyst life. There exists a need to extend hydro-regeneration catalyst life and improve reliability of the process.

SUMMARY

In one aspect, there is provided a noble metal catalyst for hydro-regeneration of a deactivated ionic liquid catalyst containing conjunct polymer, wherein the noble metal catalyst comprises a Group VIII noble metal hydrogenation component on a support having mesopores and macropores; wherein the noble metal catalyst has an average pore size of 20 to 1,000 nm (0.02 to 1 μm), a total pore volume of greater than 0.80 cc/g, and a macropore volume of 0.10 to 0.50 cc/g.

In another aspect, there is provided a hydro-regeneration catalyst system, comprising: (a) a first graded bed comprising a guard bed material having 10 μm (10,000 nm) or larger with pores with an average pore diameter of 100 to 1,000 μm (100,000 to 1,000,000 nm); and (b) a second graded bed, fluidly connected to the first graded bed, comprising a first noble metal catalyst comprising a first Group VIII noble metal hydrogenation component on a first support having mesopores and macropores; wherein the first noble metal catalyst has an average pore diameter of 20 to 1,000 nm (0.02 to 1 μm), a total pore volume of greater than 0.80 cc/g, and a macropore volume of 0.10 to 0.50 cc/g. The hydro-regeneration catalyst system may further comprise (c) a third graded bed, fluidly connected and following the second graded bed, comprising a second noble metal catalyst comprising a second Group VIII noble metal hydrogenation component on a second support having mesopores; wherein the second noble metal catalyst has an average pore diameter of less than 20 nm (0.02 μm) and macropore volume less than 0.10 cc/g.

In a further aspect, there is provided a process for hydro-regeneration of a deactivated ionic liquid catalyst containing conjunct polymer, the process comprising: (a) contacting the deactivated ionic liquid catalyst containing the conjunct polymer with a first noble metal catalyst under first hydrogenation conditions to form a first stream comprising conjunct polymer-depleted ionic liquid catalyst, wherein the noble metal catalyst comprises a first Group VIII noble metal hydrogenation component on a first support having mesopores and macropores; wherein the first noble metal catalyst has an average pore size of 20 to 1,000 nm (0.02 to 1 μm), a total pore volume of greater than 0.80 cc/g, and a macropore volume of 0.10 to 0.50 cc/g; and (b) recovering conjunct polymer-depleted ionic liquid catalyst from the first stream.

In yet a further aspect, there is provided process for hydro-regeneration of a deactivated ionic liquid catalyst containing conjunct polymer, the process comprising the steps of: (a) contacting the deactivated ionic liquid catalyst containing the conjunct polymer with a first noble metal catalyst under first hydrogenation conditions to form a first stream comprising a conjunct polymer-depleted ionic liquid catalyst having a first conjunct polymer content, wherein the first noble metal catalyst comprises a first Group VIII noble metal hydrogenation component on a first support having mesopores and macropores; wherein the first noble metal catalyst has an average pore size of 20 to 1,000 nm (0.02 to 1 μm), a total pore volume of greater than 0.80 cc/g, and a macropore volume of 0.10 to 0.50 cc/g; (b) contacting at least a portion of the first stream comprising a conjunct polymer-depleted ionic liquid catalyst with a second noble metal catalyst under second hydrogenation conditions to form a second stream comprising a conjunct polymer-depleted ionic liquid catalyst having a second conjunct polymer content, wherein the second noble metal catalyst comprises a second Group VIII noble metal hydrogenation component on a second support having mesopores; wherein the noble metal catalyst has an average pore diameter of less than 20 nm (0.02 μm); and (c) recovering conjunct polymer-depleted ionic liquid catalyst from the second stream.

In still yet a further aspect, there is provided a guard bed system for removing organic oligomer, coke, and metal impurities from a deactivated ionic liquid catalyst stream, the guard bed system comprising (a) a first guard bed comprising a first adsorbent material having 10 μm (10,000 nm) or larger pores with an average pore diameter of 100 to 1000 μm (100,000 to 1,000,000 nm); and (b) a second guard bed comprising a second adsorbent having mesopores and macropores with an average pore diameter of 20 to 1,000 nm (0.02 to 1 μm), wherein the second guard bed is fluidly connected to first guard bed. The system is configured such that in use, the deactivated ionic liquid catalyst contacts the first guard bed before contacting the second guard bed.

DETAILED DESCRIPTION

Introduction

Figure 1A:
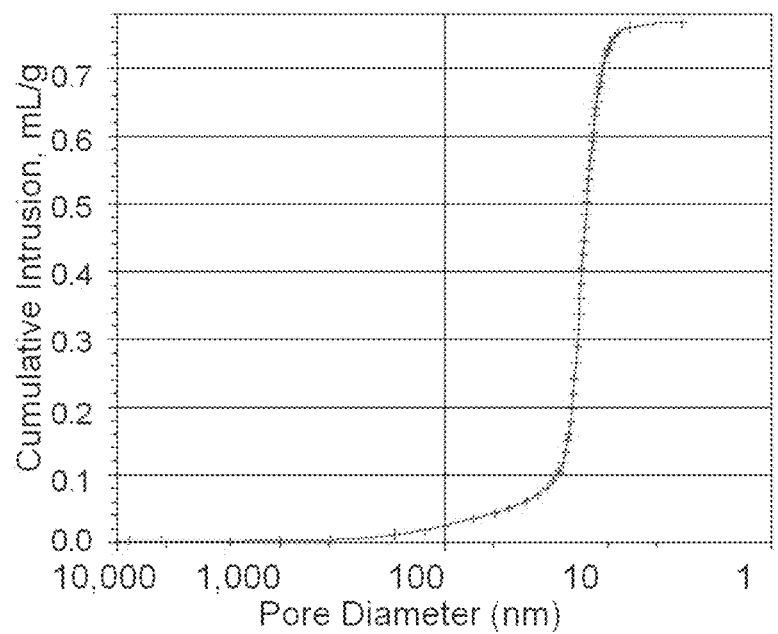
FIGS. 1(a) and (b) are graphical depictions of the cumulative intrusion and differential intrusion, respectively, during Hg porosimetry of Catalyst A.

The term "deactivated ionic liquid catalyst" refers to ionic liquid catalysts that have been used in hydrocarbon conversion processes, and in which conjunct polymers have formed. The conjunct polymer is retained in the ionic liquid, and it cannot be separated from the ionic liquid by washing with a solvent. Deactivated ionic liquid catalysts include partially or completely deactivated ionic liquid catalysts.

The term "hydro-regeneration" refers to a process in which a deactivated ionic liquid feedstock is brought into contact with hydrogen and a catalyst, at a higher temperature and pressure, for the purpose of at least partially restoring the activity of the ionic liquid for the process for which the purpose is intended.

The term "regenerated ionic liquid catalyst" refers to an ionic liquid catalyst that has regained enough activity to be efficient in a specified process. Such efficiency is determined by individual process parameters.

The term "noble metal" refers to metals that are highly resistant to corrosion and/or oxidation. Group VIII noble metals include ruthenium (Ru), osmium (Os), rhodium (Rh), iridium (Ir), palladium (Pd), and platinum (Pt).

The terms "macroporous," "mesoporous," and "microporous" are known to those of ordinary skill in the art and are used herein in consistent fashion with their description in the International Union of Pure and Applied Chemistry (IUPAC) Compendium of Chemical Terminology, Version 2.3.2, Aug. 19, 2012 (informally known as the "Gold Book"). Generally, microporous materials include those having pores with cross-sectional diameters of less than 2 nm (0.002 μm). Mesoporous materials include those having pores with cross-sectional diameters of from 2 to 50 nm (0.002 to 0.05 μm). Macroporous materials include those having pores with cross-sectional diameters of greater than about 50 nm (0.05 μm). It will be appreciated that a given material or composition may have pores in two or more such size regimes, e.g., a particle may comprise macroporosity, mesoporosity and microporosity.

All ASTM standards referred to herein are the most current versions as of the filing date of the present application.

Ionic Liquid Catalyst

The ionic liquid catalyst can be any ionic liquid. There can be one or more ionic liquids. The ionic liquid comprises an organic cation and an anion. Suitable cations include nitrogen-containing cations and phosphorus-containing cations. Representative organic cations may include the following:

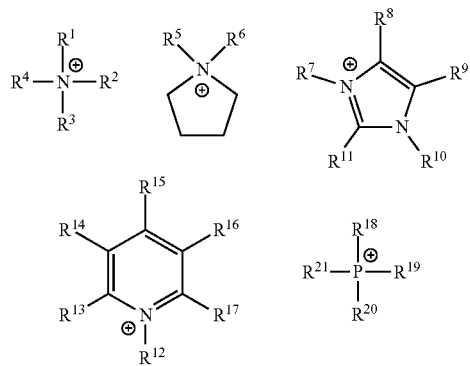

where $R^1$ to $R^{21}$ are independently selected from hydrogen, $C_1$-$C_{20}$ hydrocarbons (e.g., $C_1$-$C_8$ hydrocarbons), and halogens.

The anion can be derived from halides, sulfates, bisulfates, nitrates, sulfonates, fluoroalkanesulfonates, halometallates and combinations thereof. The anion is typically derived from metal and non-metal halides, such as metal and non-metal chlorides, bromides, iodides, fluorides, or combinations thereof. Combinations of anions include mixtures of two or more metal halides (e.g., $AlCl_4^-$ and $BF_4^-$), and mixtures of two or more halides with a single metal (e.g., $AlCl_3Br$).

In some embodiments, the anion is a halometallate. The halometallate anion can be metal chlorides, bromides, iodides, fluorides, or combinations thereof. Suitable metals in the halometallate include aluminum, iron, copper, zinc, and gallium. Examples of suitable halometallates include $AlX_4^-$, $Al_2X_7^-$, and $Al_3X_{10}^-$, where X is a halogen independently selected from the group consisting of F, Cl, Br, and I. Desirably, the anion is a chloroaluminate.

Suitable chloroaluminate ionic liquid catalysts include alkylimidazolium chloroaluminates such as 1-ethyl-3-methylimidazolium heptachlorodialuminate [emim$^+$][$Al_2Cl_7^-$], alkylpyridinium chloroaluminates such as N-butylpyridinium heptachlorodialuminate [NBuPy$^+$][$Al_2Cl_7^-$], and alkylphosphonium chloroaluminates such as tributylhexylphosphonium heptachlorodialuminate [TBHP$^+$][$Al_2Cl_7^-$].

Deactivated Ionic Liquid Catalyst

Acidic ionic liquid catalysts are used in various hydrocarbon conversion processes, such as alkylation, olefin oligomerization, isomerization and disproportionation reactions. During the hydrocarbon conversion process, the catalyst may be deactivated due to accumulation of impurities.

One of the impurities that can accumulate in the ionic liquid is conjunct polymer. Conjunct polymers are polyunsaturated cyclic, polycyclic and acyclic molecules formed by concurrent acid-catalyzed reactions including, amongst others, alkylation, polymerization, cyclization, and hydride transfer reactions. These conjunct polymers deactivate the ionic liquid catalyst by forming complexes with the Lewis acid portion of the ionic liquid catalyst via their double bonds. For example, as aluminum trichloride in aluminum trichloride-containing ionic liquid catalysts becomes complexed with conjunct polymers, the activity of these ionic liquid catalysts becomes impaired or at least compromised. Conjunct polymers may also become chlorinated and through their chloro groups may interact with aluminum trichloride in aluminum-trichloride containing catalysts and therefore reduce the overall activity of these catalysts or lessen their effectiveness as catalysts for their intended purpose. Conjunct polymers cannot be separated from the ionic liquid by washing with a solvent.

The deactivated ionic liquid may comprise greater than 5 wt. % (e.g., 10 to 30 wt. %) of conjunct polymer.

The deactivated acidic ionic liquid may also comprise of corrosion product metals. The corrosion product metals can leach from the metal surfaces of processing equipment that the ionic liquid contacts and become dissolved in the deactivated ionic liquid. Examples of materials used for processing equipment handling ionic liquids may include steel, titanium, nickel-copper alloys, and nickel-based super alloys.

The deactivated ionic liquid may comprise from 100 to 50,000 ppm corrosion product metals. The deactivated ionic liquid may comprise less than 10,000 ppm (e.g., from 10 to 5,000 ppm) corrosion product metals. The deactivated ionic liquid may comprise from 10 to 2,500 ppm nickel, wherein the nickel is a corrosion product metal. The term "ppm" as used herein is defined as parts per million expressed by weight (e.g., 1 ppm=1 mg/kg).

Ionic Liquid Catalyst Hydro-Regeneration

The deactivated ionic liquid catalyst can be regenerated in a non-destructive manner by freeing up the Lewis acid (e.g., $AlCl_3$) from the conjunct polymer—Lewis acid complex. The deactivated ionic liquid catalyst may be regenerated by contacting the deactivated ionic liquid catalyst with hydrogen and a noble metal catalyst in a regeneration reactor under effective hydrogenation conditions ("hydro-regeneration"). During the hydro-regeneration process, the double bonds of the conjunct polymers are saturated and are no longer able to be coordinated or complexed to the Lewis acid. No longer bound by conjunct polymers, the Lewis acid is then available to take part in catalytic reactions.

Hydrogenation conditions may include a temperature of −20° C. to 400° C. (e.g., 50° C. to 350° C.), a total pressure of 100 kPa to 34 MPa (e.g., 250 kPa to 17 MPa), and a residence time of 0.1 minute to 24 hours (e.g., 10 minutes to 12 hours). The ratio of feed to catalyst during the hydrogenation can vary from 0.1 to 10 vol/vol/hour. A normal hydrocarbon (e.g., a $C_3$-$C_{15}$ normal hydrocarbon or $C_6$ hydrocarbon such as n-hexane) can optionally be used as a solvent in the reactor. The temperature, pressure and residence time may be selected to achieve a desired level of activity for the regenerated ionic liquid catalyst.

The reaction product is withdrawn from the regeneration reactor and sent to a separator. This mixture is then separated into two streams, one stream comprising hydrogen and light hydrocarbons in a gas phase, a second liquid stream comprising inert hydrocarbons and/or reduced conjunct polymers and regenerated ionic liquid catalyst. The recovered regenerated ionic liquid catalyst is recycled to a hydrocarbon conversion reactor for use in hydrocarbon conversion reactions.

It is not necessary to regenerate the entire charge of deactivated ionic liquid catalyst. In some instances, only a portion of the deactivated ionic liquid catalyst charge is regenerated (i.e., only as much ionic liquid catalyst is regenerated as is necessary to maintain a desired level of catalyst activity in the process in which the ionic liquid is used as the catalyst).

The hydro-regeneration can be performed either in a stirred reactor or a fixed bed reactor. For ease of operation, a fixed bed reactor is preferred even though the fixed bed regenerator reactor is more susceptible to plugging from coking, deposits of corrosion product metals and decomposition products derived from feed contaminants.

Fresh (i.e., unused) ionic liquid catalyst may be added to the reactor during the hydro-regeneration process to dissolve any undesirable by-products. These by-products may accumulate on the external surface of the noble metal catalyst bed resulting in higher-than-normal pressure differentials in the reactor due to higher flow resistance to the ionic liquid catalyst.

Noble Metal Catalyst

The noble metal catalyst includes a Group VIII noble metal hydrogenation component supported on a macroporous support.

The Group VIII noble metal hydrogenation component may be selected from Ru, Os, Rh, Ir, Pd, Pt, and combinations thereof (e.g., Pd, Pt, and combinations thereof). The Group VIII noble metal hydrogenation component may be incorporated into the hydrogenation catalyst by methods known in the art, such as ion exchange, impregnation, incipient wetness or physical admixture. After incorporation of the Group VIII noble metal, the catalyst is usually calcined at a temperature between 200° C. to 500° C.

The amount of Group VIII noble metal in the noble metal catalyst may be from 0.05 to 2.5 wt. % (e.g., 0.05 to 1 wt. %, 0.05 to 0.5 wt. %, 0.05 to 0.35 wt. %, 0.1 to 1 wt. %, 0.1 to 0.5 wt. %, or 0.1 to 0.35 wt. %) of the total weight of the catalyst.

Suitable supports include alumina, silica, silica-alumina, zirconia, titania, and combinations thereof. Alumina is a preferred support. Suitable aluminas include γ-alumina, η-alumina, pseudoboehmite, and combinations thereof.

The macroporous support may contain mesopores and macropores in 10 to 10,000 nm (0.01 to 10 μm) range. The mesopore sizes are predominantly in 10 to 50 nm (0.01 to 0.05 μm) range and macropore sizes in 100 to 5,000 nm (0.1 to 5 μm) range. The mean average mesopore diameter is in the range of 10-50 nm (0.01-0.05 μm), preferably in the range of 10 to 20 nm (0.01 to 0.02 μm). The mean average macropore diameter is in the range of 100 to 1,000 nm (0.1 to 1 μm), preferably in the range of 200 to 5,000 nm (0.2 to 0.5 μm).

For the purposes of this disclosure, rather than reporting two mean pore diameters for the support with meso and macroporous pores, the average pore diameter is estimated using the total pore volume and the total surface area for effective comparison with other materials.

The noble metal catalyst may have an average pore diameter of 20 to 1,000 nm (0.02 to 1 μm) (e.g., 20 to 800 nm, 20 to 500 nm, 20 to 200, 25 to 800, 25 to 500, or 25 to 250 nm).

The noble metal catalyst may have a macropore volume of at least 0.10 cc/g (e.g., 0.10 to 0.50 cc/g, 0.10 to 0.45 cc/g, 0.10 to 0.40 cc/g, 0.15 to 0.50 cc/g, 0.15 to 0.45 cc/g, 0.15 to 0.40 cc/g, 0.20 to 0.50 cc/g, 0.20 to 0.45 cc/g, or 0.20 to 0.40 cc/g).

The noble metal catalyst may have a total pore volume of greater than 0.80 cc/g (e.g., at least 0.85 cc/g, at least 0.90 cc/g, at least 0.95 cc/g, >0.80 to 1.5 cc/g, >0.80 to 1.25 cc/g, >0.80 to 1.10 cc/g, 0.85 to 1.5 cc/g, 0.85 to 1.25 cc/g, 0.85 to 1.10 cc/g, 0.90 to 1.50 cc/g, 0.90 to 1.25 cc/g, 0.90 to 1.10 cc/g, 0.95 to 1.50 cc/g, 0.95 to 1.25 cc/g, or 0.95 to 1.10 cc/g).

The fraction of macropore volume relative to the total pore volume of the noble metal catalyst may range from 10 to 50% (e.g., 15 to 50%, 15 to 45%, 15 to 40%, 20 to 50%, 20 to 45%, 20 to 40%, 25 to 50%, 25 to 45%, or 25 to 40%).

The catalyst (and support) can be prepared to include macropores by, for example, utilizing a pore former when preparing the catalyst (and support), utilizing a support that contains such macropores (i.e., a macroporous support), or exposing the catalyst to heat (in the presence or absence of steam). A pore former is a material capable of assisting in the formation of pores in the catalyst support such that the support contains more and/or larger pores than if no pore former was used in preparing the support. The methods and materials necessary to ensure suitable pore size are generally known by persons having ordinary skill in the art of preparing catalysts.

The catalyst (and support) may be in the form of beads, monolithic structures, trilobes, extrudates, pellets or irregular, non-spherical agglomerates, the specific shape of which may be the result of forming processes including extrusion.

The macroporous noble metal catalyst in this disclosure may be further characterized by an increased useful catalyst lifespan when compared to an otherwise similar catalyst having an average pore diameter of less than 20 nm (0.02 μm), a total pore volume of less than 0.8 cc/g, and a macropore volume of less than 0.1 cc/g. Herein, the useful catalyst lifespan refers to the time between when the catalyst is placed in service and when one or more parameters indicate that the catalyst should be removed from service (for example, reaching the end-of-run temperature, reaching a temperature close to reactor metallurgical limits or if the operation is no longer economical). The macroporous noble metal catalysts may exhibit a useful catalyst lifespan that is increased by at least 10% (at least 20% or at least 30%) when compared to an otherwise similar catalyst having an average pore diameter of less than 20 nm (0.02 μm), a total pore volume of less than 0.8 cc/g, and a macropore volume of less than 0.1 cc/g.

Guard Bed

One or more guard beds containing adsorbent material with appropriate pore size may be used to protect the noble metal catalyst from impurities (e.g., organic oligomers, coke, corrosion product metals of Group 1-12 metals such as one or more of Ti, Cr, Mn, Fe, Ni, and Cu) contained in the ionic liquid feed stream. The guard bed can be placed in the same vessel as the vessel in which ionic liquid catalyst regeneration takes place or it can be in a different vessel. Whether in the same or different vessels, the guard bed is placed upstream of the noble metal catalyst. The benefit of the noble metal catalyst and guard bed being in separate vessels is that there can be independent control of process conditions such as temperature and pressure to ensure optimal rates for both steps. Moreover, this arrangement gives flexibility in handling of unanticipated plant upsets and guard material change out without shutting down the overall process. The benefit of the noble metal catalyst and guard bed being in the same vessel is that arrangement for the regeneration process is more compact and easier to construct. More than one guard bed having the same or different composition can be used. The presence of more than one guard bed may give a longer run length.

Suitable guard bed materials are known in the art and include, for example, carbon, silica, alumina, silica-alumina, ceramic, and/or resins. Multiple guard bed materials with different porosities may be used to capture impurities with varying particle sizes.

In one embodiment, a guard bed material contains mesopores and macropores, with an average pore diameter in the range of 20 to 1,000 nm (0.02 to 1 μm) (e.g., 20 to 800 nm (0.02 to 0.8 μm), or 20 to 500 nm (0.02 to 0.5 μm).

In another embodiment, another guard bed material contains 10 μm or larger (e.g., 100 μm or larger) pores. In one embodiment, the average pore diameter of the guard bed material may range from 100 to 1000 μm (e.g., 150 to 1000 μm, or 250 to 800 μm).

In one embodiment, a guard bed may comprise a first adsorbent material having an average pore diameter of at least 100 μm (e.g., 100 to 1000 μm, or 250 to 800 μm) and a second adsorbent material having macropores with an average pore diameter of 0.02 to 1 μm (20 to 1000 nm), e.g., 0.05 to 0.75 μm (50 to 750 nm). The volume ratio of the first adsorbent material to the second adsorbent material may range from 10:1 to 1:4.

The relative amount of adsorbent guard bed material to the noble metal catalyst may range from 1:10 to 2:1 volume ratio (e.g., 1:5 to 1:1).

A guard bed such as described herein above may also be arranged upstream of a hydrodechlorination catalyst to protect the hydrodechlorination catalyst from contaminants that may be present in the feed to this catalyst.

Hydro-Regeneration Reactor Bed Arrangement

Several noble metal catalysts may be layered together to further improve the performance of the hydro-regeneration unit. For example, a second noble metal catalyst may be a component of a catalyst system for ionic liquid hydro-regeneration and may be placed downstream from the first noble metal catalyst described herein above. In one embodiment, the second noble metal catalyst includes a Group VIII noble metal hydrogenation component supported on a support having an average pore size of less than 20 nm (0.02 μm) (e.g., 3 to 20 nm). The Group VIII noble metal hydrogenation component may be selected from Ru, Os, Rh, Ir, Pd, Pt, and combinations thereof (e.g., Pd, Pt, and combinations thereof). The amount of Group VIII noble metal in the second noble metal catalyst may be from 0.05 to 2.5 wt. % (e.g., 0.05 to 1 wt. %, 0.05 to 0.5 wt. %, 0.05 to 0.35 wt. %, 0.1 to 1 wt. %, 0.1 to 0.5 wt. %, or 0.1 to 0.35 wt. %) of the total weight of the catalyst.

The first noble metal catalyst and the second noble metal catalyst may be positioned in the same reactor or in separate reactors. The first noble metal catalyst and the second noble metal catalyst may be arranged in separate beds in the same reactor.

Regenerated Ionic Liquid Catalyst

After hydro-regeneration, the amount of conjunct polymer in the regenerated ionic liquid catalyst is reduced by at least 10% (e.g., at least 25%, at least 50%, at least 75%, or at least 90%) compared to the original amount of the conjunct polymer in the deactivated ionic liquid catalyst.

The regenerated ionic liquid catalyst may comprise 5 wt. % or less (e.g., 2.5 wt. % or less, or 1.5 wt. % or less) conjunct polymer. In one embodiment, the regenerated ionic liquid catalyst may comprise from 0.05 to 10 wt. % conjunct polymer.

EXAMPLES

The following illustrative examples are intended to be non-limiting.

Example 1

Ionic Liquid Catalyst Comprising Anhydrous Metal Halide

N-butylpyridinium heptachlorodialuminate was the ionic liquid catalyst used in the process examples. This ionic liquid catalyst had a density of 1.34 g/cc with the composition shown in Table 1.

TABLE 1

Composition of Fresh and Used Ionic Liquid Catalyst Composition

|  | Fresh Ionic Liquid Catalyst | Used Ionic Liquid Catalyst[a] |
|---|---|---|
| Al, wt. % | 11.18 | 9.78 |
| Cl, wt. % | 56.5 | 49.2 |
| C, wt. % | 25.95 | 28.96 |
| H, wt. % | 3.29 | 3.85 |
| N, wt. % | 3.32 | 3.21 |
| O, wt. % | 0.05 | 0.78 |
| Cr, ppm | <10 | 100 |
| Cu, ppm | <10 | 2747 |
| Fe, ppm | 17 | 1915 |
| Mn, ppm | <10 | 124 |
| Mo, ppm | <10 | 8 |

TABLE 1-continued

Composition of Fresh and Used Ionic Liquid Catalyst Composition

|  | Fresh Ionic Liquid Catalyst | Used Ionic Liquid Catalyst[a] |
|---|---|---|
| Ni, ppm | <10 | 882 |
| S, ppm | <10 | 505 |
| Sum, wt. % | 100.29 | 96.41 |

[a] 99 days-on-stream

Example 2

Preparation of Catalyst for Ionic Liquid Catalyst Hydro-Regeneration (Catalyst A)

A noble metal impregnated alumina catalyst (Catalyst A) was prepared per the following procedure. An alumina extrudate support sample was prepared. The sample was made by extrusion of pseudoboehmite followed by drying and calcination at 1100° F. (593.3° C.) for 1 hour. The alumina support sample had 200 $m^2$/g of surface area by $N_2$ adsorption and 0.77 cc/g of total pore volume by Hg adsorption. Hg adsorption revealed that the sample contained only minor amount of macropores, 0.02 cc/g of macropore pore volume from the pore diameter exceeding 100 nm (0.1 μm).

Solutions of tetraammineplatinum(II) dinitrate and tetraamminepalladium(II) dinitrate were prepared at a concentration corresponding to 0.18 wt. % Pt and 0.36 wt. % Pd loadings respectively on the finished catalyst; a total impregnation solution volume equivalent to 105% water pore volume was used. The noble metals were loaded via incipient wetness impregnation. The impregnated extrudates were dried at 250° F. (121.1° C.), followed by calcination at 750° F. (398.9° C.) for 1 hour.

Figure 1B:
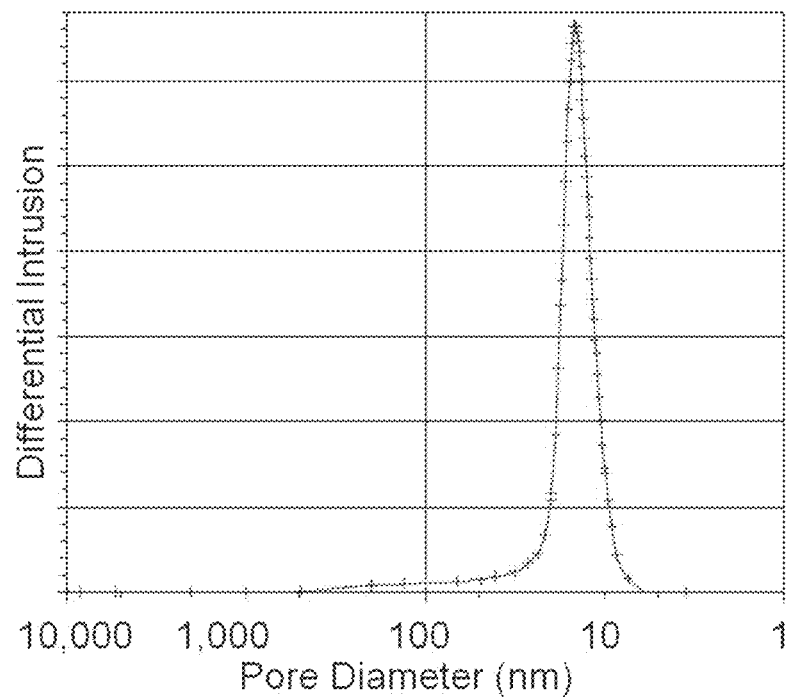

The properties of Catalyst A are summarized in Table 2. FIGS. 1(a) and 1(b) show the pore size distribution as determined by mercury porosimetry. Catalyst A contains 0.77 cc/g total pore volume and 14.7 nm (0.0147 μm) average pore diameter, and the pore size distribution was primarily composed of mesopores with the macropore volume accounting for only 3% of the total pore volume.

TABLE 2

Physical Properties of Catalysts and Adsorbents for Extended Operation with Used Ionic Liquid Catalyst

|  | Catalyst A Base Case | Catalyst B | Catalyst C | Adsorbent I | Adsorbent II |
|---|---|---|---|---|---|
| Support | Alumina extrudates | Alumina beads | Alumina extrudates | Alumina beads | Ceramic pellets of silica-alumina |
| Impregnated metals, wt. % | 0.18% Pt 0.36% Pd | 0.09% Pt 0.18% Pd | 0.09% Pt 0.18% Pd | None | None |
| Surface Area[a], $m^2$/g | 189 | 155 | 130 | 159 | 0.2[b] |
| Total Pore Volume, cc/g | 0.77[c] | 1.04[c] | 0.99[c] | 1.05[c] | 1.70[d] |
| Macropore Pore Volume[e], cc/g | 0.02 | 0.39 | 0.30 | 0.40 | ~0 |
| % Macropore/ Total Pores[f] | 3 | 38 | 30 | 38 | ~0 |
| Average Pore Diameter, nm[g] | 14.7 | >20 | 27.0 | >20 | 600,000 |

TABLE 2-continued

Physical Properties of Catalysts and Adsorbents for
Extended Operation with Used Ionic Liquid Catalyst

|  | Catalyst A Base Case | Catalyst B | Catalyst C | Adsorbent I | Adsorbent II |
|---|---|---|---|---|---|
| Characteristics of the pore size distribution in the catalyst and adsorbent | Mostly mesopores in 10-20 nm (0.01-0.02 μm) range pores | Contains mesopores and macropores in 10-10,000 nm (0.01-10 μm) range pores | Contains mesopores and macropores in 10-10,000 nm (0.01-10 μm) range pores | Contains mesopores and macropores in 10-10,000 nm (0.01-10 μm) range pores | Contains 10 μm or larger pores with 10-2,000 μm range pores |
| Particle density[h], g/cc | 0.93 | 0.74 | 0.84 | 0.75 | 2.4 |
| Bulkdensity[i], g/cc | 0.55 | 0.49 | 0.52 | 0.51 | 0.27 |

[a]Determined by nitrogen adsorption using ASTM D3663 established from the Brunauer-Emmet-Teller method described by Brunauer et al, J. Am. Chem. Soc. 1938, 60, 309-319.
[b]The surface area of the Adsorbent II was very low since the material contained no micropores or mesopores. Adsorbent II contained only 10-2,000 μm (10,000-2,000,000 nm) size pores.
[c]Measured by mercury porosimetry in accordance with ASTM D4284.
[d]For adsorbents containing pores larger than 10 μm, like Adsorbent II, the Hg adsorption technique could not be used for the pore volume measurement since the pores were not completely filled with mercury liquid. The pore volume and particle density were estimated with water by pore filling of a single pellet.
[e]"Macropore Volume" is the pore volume associated with 100-10,000 nm (0.1-10 μm) pore diameters, as measured by mercury porosimetry.
[f]The "% of Macropore/Total Pores" is the fraction of macropore volume relative to the total pore volume.
[g]Average pore diameter was calculated value from Hg porosimetry intrusion (4V/A) data where V is the total pore volume and A is the total surface area coming from all pores.
[h]Particle density (D) was obtained by applying the formula D = M/V where M is the weight and V is the volume of the catalyst sample. The volume was determined by measuring volume displacement following submersion of the sample under mercury at 28 mm Hg vacuum pressure.
[i]Bulk density was the vessel loading density of the catalyst or adsorbent medium (compacted density with vibration per ASTM D4180).

Example 3

Continuous Ionic Liquid Alkylation Process of $C_3/C_4$ Olefin and Isobutane to Make Alkylate Gasoline in Combination with Hydro-Regeneration Process Refinery isobutane containing 85% isobutane and 15% n-butane was used for this study, following drying of the refinery isobutane with 13x molecular sieve. A refinery olefin stream containing $C_3$ and $C_4$ olefins ($C_3/C_4$ Olefin) from a Fluid Catalytic Cracking Unit (FCC unit) was dried with 13x molecular sieve and isomerized with a Pd/Al$_2$O$_3$ catalyst at 150° F. (65.6° C.), and 250 psig (1,724 kPa) in the presence of hydrogen to produce isomerized $C_3$ and $C_4$ olefin feed with the composition shown in Table 3. The feed contained <1 ppm water and <10 ppm oxygenates. The moisture content was measured by an on-line moisture analyzer. The oxygenate content was measured by Gas Chromatography according to ASTM D7423.

TABLE 3

Composition of Olefin Feed

| Composition | Mole % |
|---|---|
| Propane, $C_3$ | 13.3 |
| Propylene, $C_{3=}$ | 25.4 |
| 1-Butene, 1-$C_{4=}$ | 2.3 |
| 2-Butene, 2-$C_{4=}$ | 16.2 |
| Isobutylene, i-$C_{4=}$ | 6.7 |
| n-Butane, n-$C_4$ | 12.4 |
| Isobutane, i-$C_4$ | 22.2 |
| $C_{5+}$ | 1.6 |
| Sum | 100.0 |

Evaluation of $C_3/C_4$ olefins alkylation with isobutane was performed in a continuously stirred tank reactor. An 8:1 molar mixture of isobutane and olefin was fed to the vigorously stirred reactor. An ionic liquid catalyst as described in Example 1 was fed to the reactor via a second inlet port targeted to occupy 5 vol. % in the reactor. A small amount of n-butyl chloride was added to produce anhydrous HCl gas in situ. The average residence time in the reactor (combined volume of feed and catalyst) was about 15 minutes. The outlet pressure was maintained at 200 psig (1,379 kPa) and the reactor temperature was maintained at 95° F. (35° C.) using a cooling coil.

The reactor effluent was separated with a coalescing separator into a hydrocarbon phase and an ionic liquid catalyst phase. The hydrocarbon phase was further separated via three distillation columns into multiple streams, including: a gas stream containing $C_{3-}$ fraction, an n-$C_4$ stream, an i-$C_4$ stream, and an alkylate stream. About 80-85% of the separated ionic liquid catalyst was recycled back to the alkylation reactor for re-use. To maintain the activity of the ionic liquid catalyst, a fraction of the separated ionic liquid catalyst was sent to a hydrogenation reactor containing solid hydro-regeneration catalyst (Catalyst A) for reduction of the conjunct polymer concentration in the ionic liquid catalyst. The conjunct polymer concentration of the ionic liquid catalyst was maintained at 3-5 wt. % with the hydrogenation process. The amount of conjunct polymer in the ionic liquid catalyst was determined using an FT-IR quantitation method described in U.S. Pat. No. 9,290,702. The continuous operation was maintained for about 200 days. During the test period, the alkylation process continuously produced alkylate gasoline with good product properties. The Research Octane Numbers (ASTM D2699) were in the range of 90-92, the Motor Octane Numbers (ASTM D2700) in the range of 89-91, the initial boiling points at between 90° F. and 100° F. (32.2° C. and 37.8° C.), 50 vol. % boiling points at between 210° F. and 215° F. (98.9° C. and 101.7° C.), and the final boiling points at between 410° F. and 420° F.

(210.0° C. and 215.6° C.). The boiling point distribution was measured according to ASTM D87.

Example 4

Impact of Extended Operation on the Used Ionic Liquid Catalyst and Impurity Build-Up The aging characteristics of the used ionic liquid catalyst in Example 3 was monitored by withdrawing samples periodically and performing elemental analysis and microscopy to determine build-up of impurities in the ionic liquid catalyst. The microscope slide samples were prepared in a glove box to minimize exposure of the ionic liquid sample to atmospheric moisture.

Since ionic liquid catalyst was used for the alkylation process with on-line regeneration, a build-up of hydrolyzed ionic liquid particles and corrosion product metals was observed in the ionic liquid. The compositional analysis of the fresh vs. used catalyst is compared in Table 1. As the ionic liquid catalyst aged, the oxygen content increased from 0.05 wt. % to 0.78 wt. % due to reaction (hydrolysis) of the ionic liquid catalyst with water and oxygenate in the hydrocarbon feeds. The content of corrosion product metals such as Cr, Cu, Fe, Ni, Mn increased from minimum to hundreds and thousands of ppm. The corrosion product metals were in the cationic state and generally dissolved in the ionic liquid catalyst, although some were precipitated as metal chloride salts.

Figure 2:
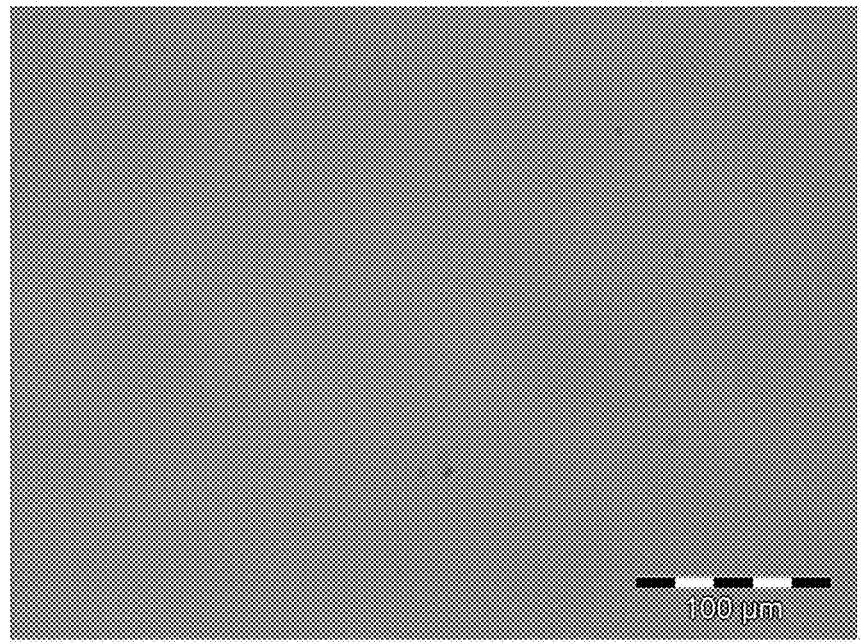
FIGS. 2(a) and (b) shows the optical microscope images of fresh and used (99 days-on-stream) ionic liquid catalyst, respectively.
Figure 2B:
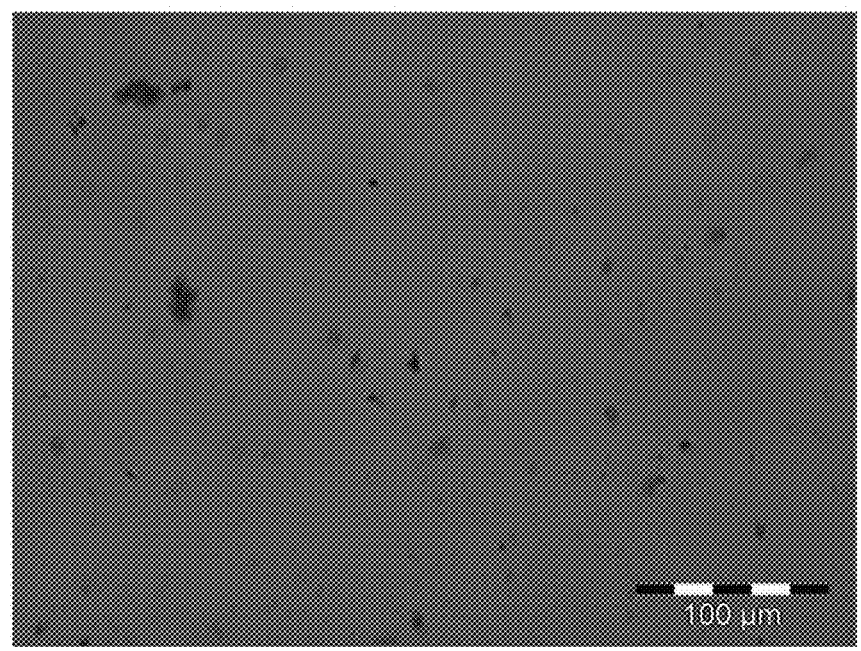

The fresh ionic liquid catalyst was a pure liquid catalyst. An optical microscope image of the fresh ionic liquid sample contained no noticeable particles as shown in FIG. 2(a). An optical microscope image of the used ionic liquid catalyst sampled from the process unit after 99 days-on-stream is shown in FIG. 2(b). While the used ionic liquid catalyst still performed well during alkylation and was regenerated adequately by the hydro-regeneration catalyst, some build-up of particulates was observed. The particles had sizes ranging from a few microns to tens of microns.

The data presented in Table 1 and the images in FIGS. 2(a) and 2(b) clearly indicate that there is a need to remove the solids and corrosion product metals from used ionic liquid catalyst in order to extend the life of the ionic liquid catalyst and reduce operating costs. Of note is that modern refineries tend to operate their process units for 2-4 years before a scheduled turn-around for a catalyst change out.

Example 5

Guard Bed for Circulating Ionic Liquid Catalyst

A guard bed was designed to capture particulates and corrosion product metals in the used ionic liquid catalyst. To maximize performance of the guard bed, the layer contained two kinds of adsorbents, Adsorbent I and Adsorbent II, with properties as shown in Table 2.

Figure 3:
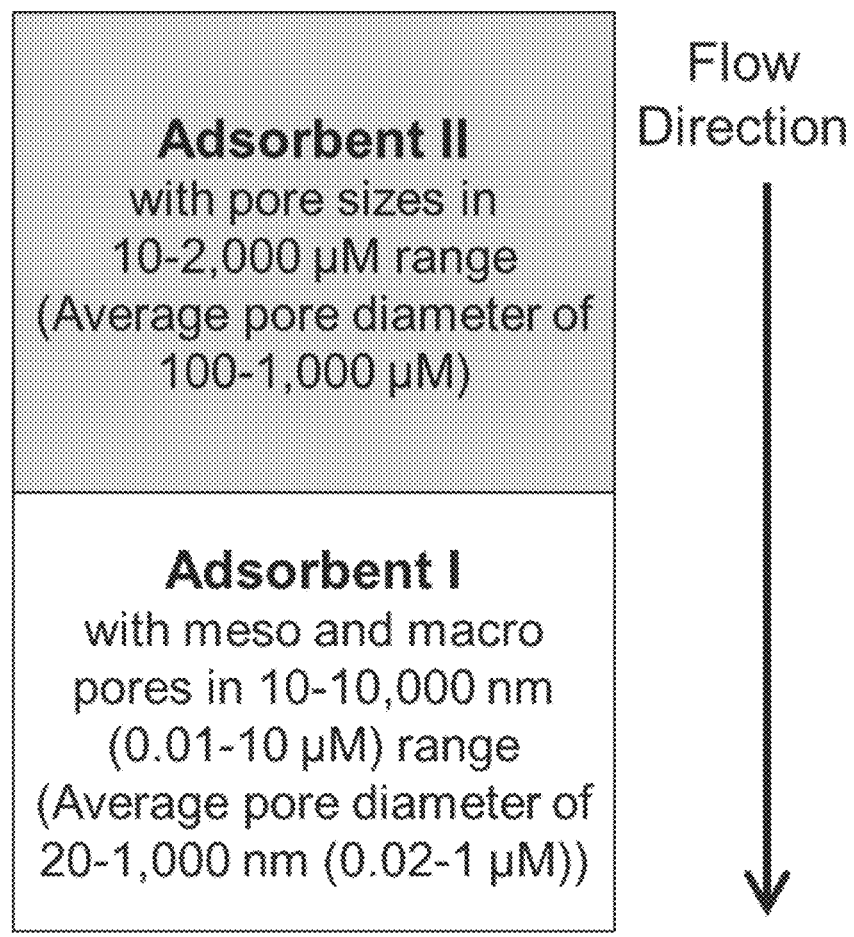
FIG. 3 shows a guard bed arrangement for circulating ionic liquid catalyst, useful in one or more embodiments of the present disclosure.

A guard bed loaded with 50 vol. % of Adsorbent I and 50 vol. % of Adsorbent II was operated in conjunction with the alkylation and hydro-regeneration reactors, as described in Example 3, for 50 days and then unloaded for analysis. FIG. 3 depicts a guard bed arrangement for circulating ionic liquid catalyst.

The spent Adsorbent I and spent Adsorbent II were analyzed for corrosion product metals by digestion-ICP. The data in Table 4 shows that Adsorbent I and Adsorbent II were effective in capturing the corrosion product metals. The adsorbents also captured hydrolyzed ionic liquid particulates from the ionic liquid catalyst since the composition of the hydrolyzed solids was similar to the ionic liquid catalyst. Although the volume of solids captured could not be measured with elemental analysis, Scanning Electron Microscopy and Energy Dispersive X-Ray analysis (EDX) revealed that the hydrolyzed particulates were also captured by Adsorbents I and II (data not shown).

TABLE 4

Capturing of Metal Impurities in Used Ionic Liquid Catalyst with a Guard Bed

|           | Used Adsorbent I | Used Adsorbent II |
|-----------|------------------|-------------------|
| Cr, wt. % | 0.05             | 0.12              |
| Cu, wt. % | 0.12             | 0.15              |
| Fe, wt. % | 0.37             | 0.82              |
| Mn, wt. % | 0.01             | 0.02              |
| Ni, wt. % | 1.04             | 2.65              |
| Sum, wt. %| 1.59             | 3.76              |

Example 6

Analysis of Spent Hydro-Regeneration Catalyst A

Figure 4:
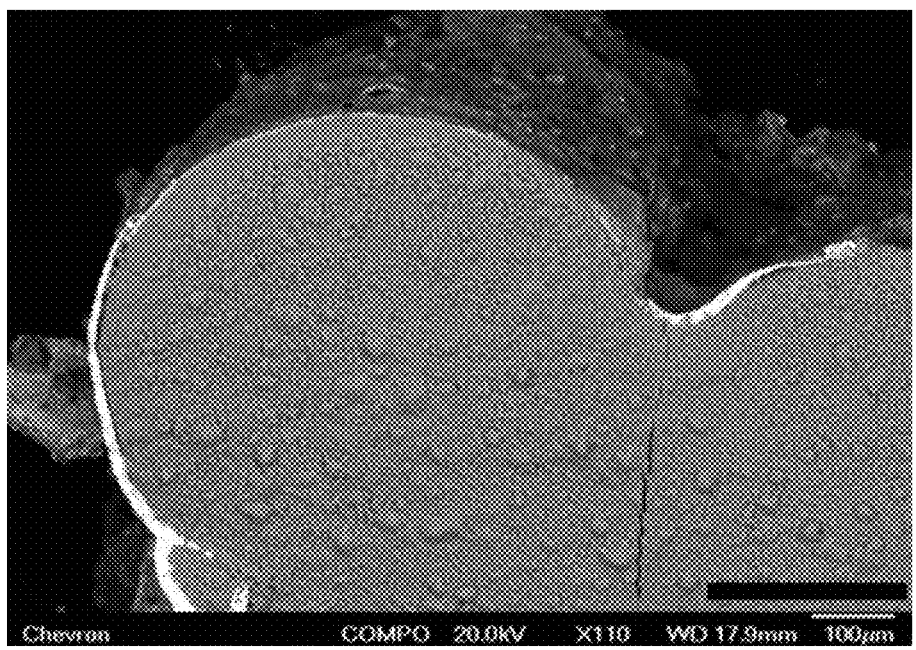
FIG. 4 shows a Scanning Electron Microscopy (SEM) back-scattering image of spent hydro-regeneration Catalyst A.

As described in Example 3, Catalyst A performed well for hydro-regeneration of used ionic liquid catalyst for a period exceeding 150 days. During unloading, the extrudate particles in the inlet section of the solid catalyst bed were fused together and difficult to unload. The spent hydrogenation catalyst sample was analyzed using Scanning Electron Microscopy. The back scattering images indicated a thin deposit of corrosion product metal chlorides (e.g., $NiCl_2$ and $FeCl_2$) was formed on the external surface of the extrudate pellets (FIG. 4). Light colored particles were corrosion product metal chlorides. An EDX scan of the center of the catalyst pellet determined corrosion product metal loadings of only 0.11 wt. % Ni, 0.26 wt. % Fe, and 0.35 wt. % Cu (only the elements of Al, Si, S, Cl, Fe, Ni, Cu were scanned and the sum of the scanned metals was normalized to 100 wt. %).

Figure 5:
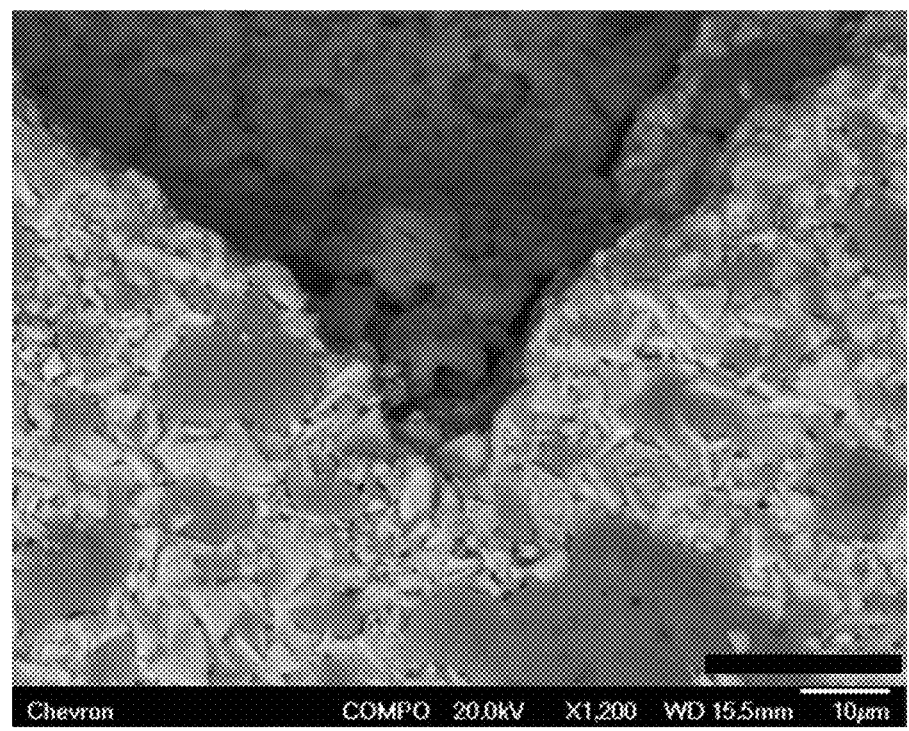
FIG. 5 shows a SEM image of metal chloride crystal deposits on spent hydro-regeneration Catalyst A.

FIG. 5 shows a SEM image of metal chloride crystal deposits on the external surface of spent hydro-regeneration Catalyst A. An EDX scan of the surface deposit showed the material was predominantly $NiCl_2$ and $FeCl_2$ with metal loadings of 20.6 wt. % Ni, 7.2 wt. % Fe and 0.1 wt. % Cu (only the elements of Al, Si, S, Cl, Fe, Ni, Cu were scanned and the sum of the scanned metals was normalized to 100 wt. %). The data clearly indicates a coating of corrosion product metals primarily on the external surface of the hydro-regeneration catalyst pellets.

Modern refineries tend to operate their process units for 2-4 years before a scheduled turn-around for a catalyst change out. Selective deposition of corrosion product metals on the external surface of catalyst pellets is highly undesirable since the corrosion product metals can fill up the interstitial void space in the hydro-regeneration catalyst bed and cause localized plugging. This in turn may lead to a severe pressure drop across the reactor bed and operability issues. Ultimately, a high pressure drop may lead to shutdown of the alkylation plant and/or shortened hydro-regeneration catalyst life. Thus, it may be desirable to improve the hydro-regeneration catalyst to be more resistant to fouling by corrosion product metals.

Example 7

Preparation of Improved Hydro-Regeneration Catalysts

An improved, fouling resistant hydro-regeneration catalyst (Catalyst B) was prepared using Adsorbent I alumina support beads per the procedure below. Adsorbent I alumina support had 159 m²/g of surface area (N₂ adsorption) and 1.05 cc/g of total pore volume (Hg adsorption). The Hg adsorption profile also revealed that the sample contained macropores and mesopores. The sample contained a substantial amount of macropores and 0.40 cc/g of macropore pore volume resulting from the pore diameter exceeding 100 nm (0.1 µm).

Solutions of tetraammineplatinum(II) nitrate and tetraamminepalladium(II) nitrate and palladium tetraammine nitrate were prepared at a concentration corresponding to 0.09 wt. % Pt and 0.18 wt. % Pd respectively on the finished catalyst; a total impregnation solution volume equivalent to 105% water pore volume was used. The noble metals were loaded via incipient wetness impregnation. The impregnated extrudates were dried at 250° F. (121.1° C.), followed by calcination at 750° F. (398.9° C.) for 1 hour.

Figure 6A:
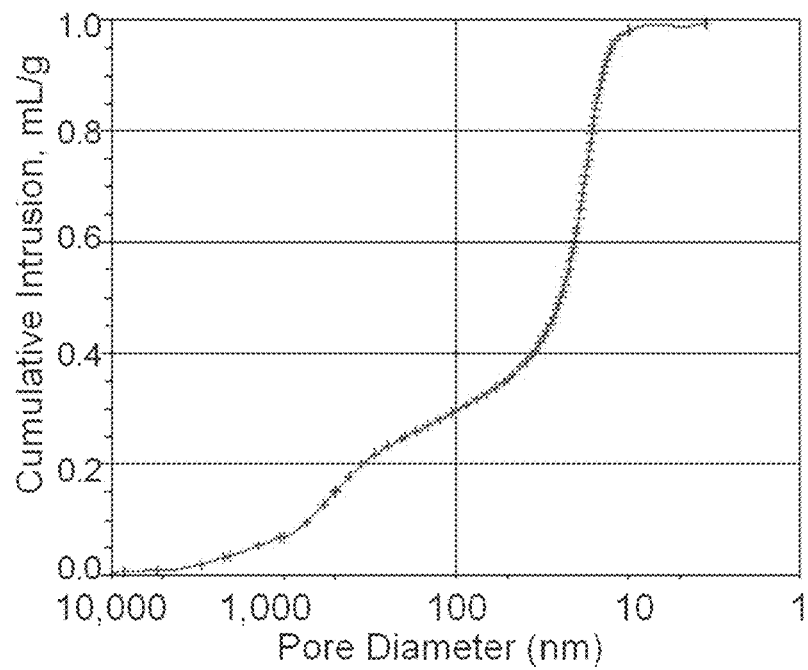
FIGS. 6(a) and (b) are graphical depictions of the cumulative intrusion and differential intrusion, respectively, during Hg porosimetry of Catalyst C.
Figure 6B:
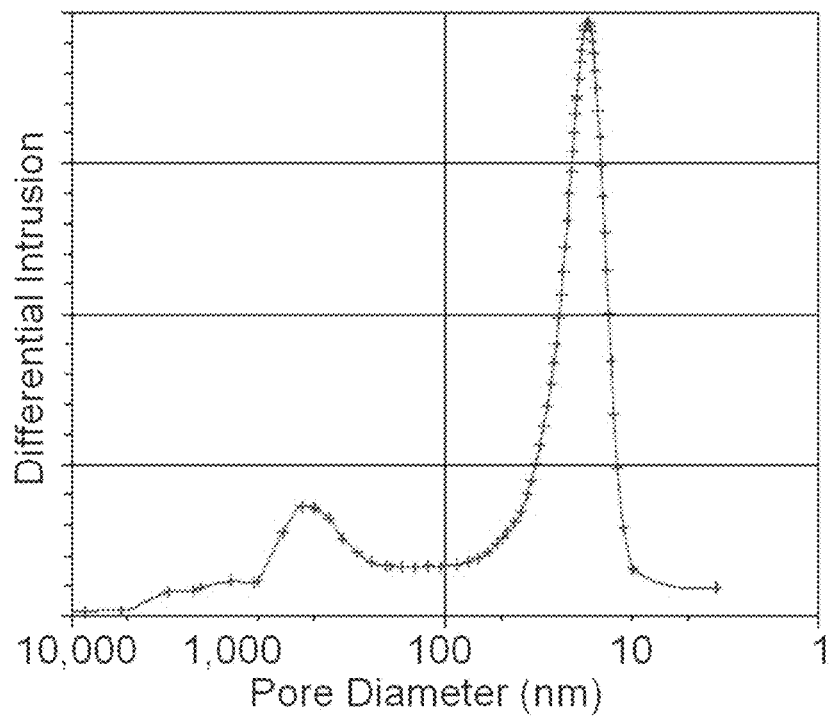

Another improved hydro-regeneration catalyst (Catalyst C) was prepared using alumina extrudates with high macropore pore volume. The noble metal impregnation procedure was identical to Catalyst B. FIGS. 6(*a*) and 6(*b*) show the distribution of pore size for Catalyst C as determined by mercury porosimetry. Catalyst C contained both mesopores and macropores with 0.99 cc/g of total pore volume by Hg adsorption. Catalyst C contained a substantial amount of macropores at >100 nm (>0.1 µm) pore diameter. The Hg adsorption profile revealed that the sample contained 0.30 cc/g of macropore pore volume resulting from the pore diameter exceeding 100 nm (0.1 µm). The average pore diameter of 27 nm (0.027 µm) was estimated from the total pore volume and the total surface area. The mean diameter of mesopores alone was 18.9 nm (0.0189 µm) and mean diameter of macropores alone was 336 nm (0.336 µm).

The properties of improved Catalyst B and Catalyst C are summarized in Table 2. Unlike Catalyst A, Catalysts B and C had a total pore volume greater than 0.8 cc/g, a macropore pore volume greater than 0.1 cc/g, an average pore diameter exceeding 20 nm, and a particle density of less than 0.85 cc/g. It is believed that the macropores in Catalysts B and C allow the corrosion product metals to superficially penetrate the pellet surfaces thus allowing the hydro-regeneration catalyst to be more resistant to fouling.

Figure 7:
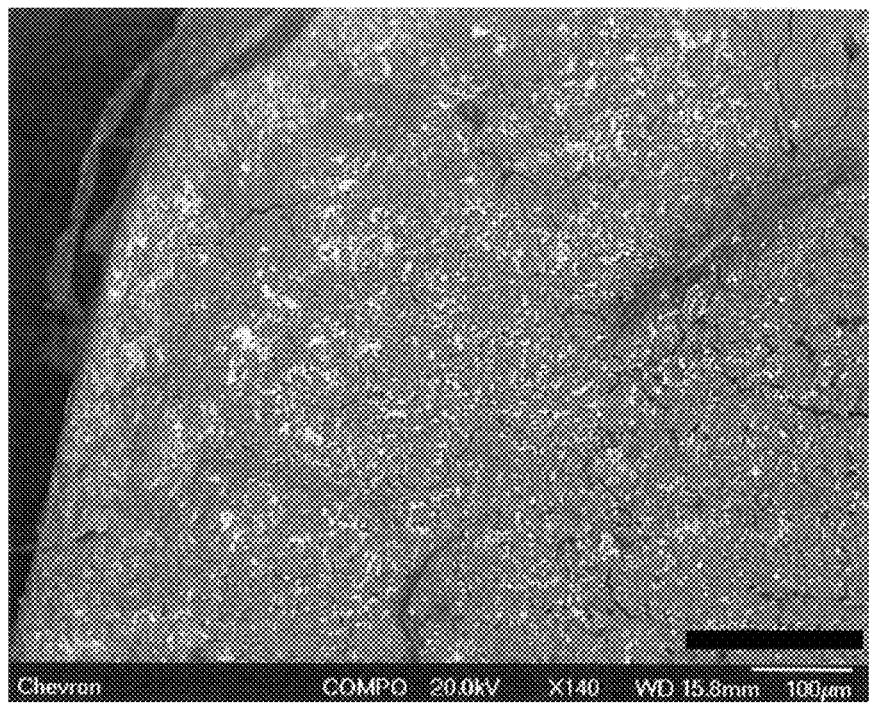
FIG. 7 shows a SEM back-scattering image of spent hydro-regeneration Catalyst B.

Catalyst B and Catalyst C were operated in conjunction with the alkylation and hydro-regeneration reactors as described in Example 3 for 45 days and then unloaded for analysis. The spent Catalysts B and C were analyzed by back-scattering Scanning Electron Microscopy. The cross-sectional image of spent Catalyst B (FIG. 7) displayed deep penetration of corrosion product metals (light colored particles) inside the pellet. An EDX scan of the catalyst core showed 13.1% Ni, 2.1% Fe, 0.2% Cr and 0.6% Cu (only the elements of Al, Si, S, CI, Cr, Fe, Ni, Cu were scanned and the sum of the scanned metals was normalized to 100 wt. %). Metal loadings in the pellet core of improved Catalyst B were an order of magnitude greater than observed on Catalyst A that previously revealed only minute amounts of Ni and Fe in the pellet core. Catalyst C also showed very high loadings of corrosion product metals in the pellet core (data not shown).

Example 8

Figure 8:
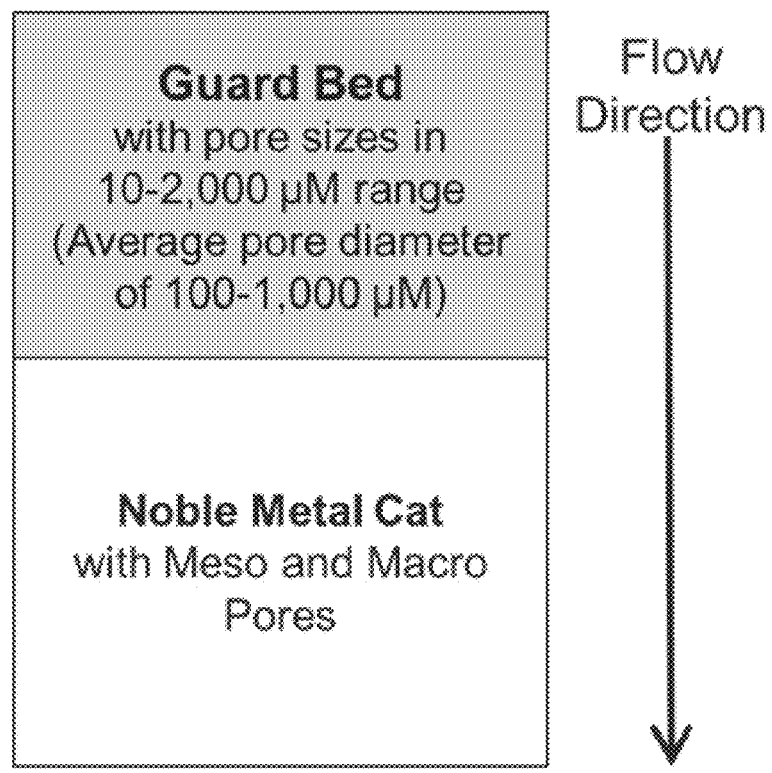
FIG. 8 shows a hydro-regeneration reactor bed arrangement, useful in one or more embodiments of the present disclosure.
Figure 9:
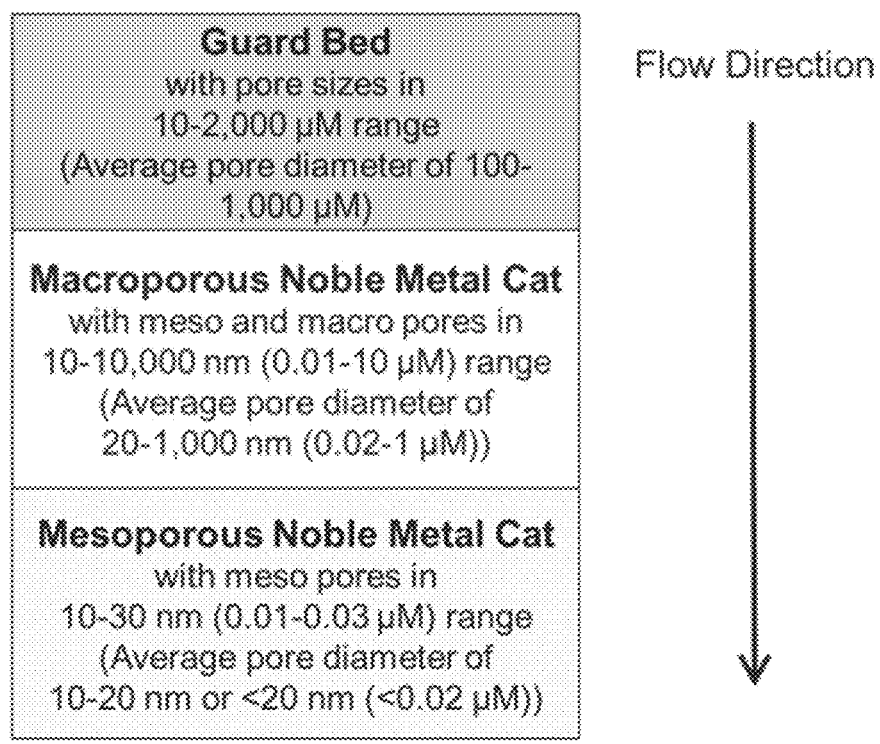
FIG. 9 shows a hydro-regeneration reactor bed arrangement, useful in one or more embodiments of the present disclosure.

Improved Hydro-Regeneration Process with Graded Adsorbent/Regeneration Catalyst Configuration In order to maximize the life of noble metal containing hydro-regeneration catalysts, a graded regeneration reactor loading concept was developed. The reactor has an Adsorbent II type of guard material at the inlet section followed by a macroporous noble metal containing hydro-regeneration catalyst. FIG. 8 illustrates one hydro-regeneration reactor bed arrangement. The flow of ionic liquid may be either upflow or downflow, but it was desirable for the largest pore material to contact the ionic liquid first. The H₂ flow to the reactor may be co-current or counter-current to the ionic liquid flow. FIG. 9 illustrates a hydro-regeneration reactor bed arrangement wherein two different noble metal catalysts are layered together to further improve the performance of the hydro-regeneration unit.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

All ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

The invention claimed is:

1. A noble metal catalyst for hydro-regeneration of a deactivated ionic liquid catalyst containing conjunct polymer, wherein the noble metal catalyst comprises a Group VIII noble metal hydrogenation component on a support having mesopores and macropores;
   wherein the noble metal catalyst has an average pore diameter of 20 to 1,000 nm (0.02 to 1 µm), a total pore volume of greater than 0.8 cc/g, and a macropore volume of 0.10 to 0.50 cc/g; and
   wherein the mesopores have a diameter from 10 to 20 nm and the macropores have a second diameter from greater than 100 to 5,000 nm.

2. The noble metal catalyst of claim 1, wherein the noble metal catalyst has an average pore diameter of from 25 to 800 nm (0.025 to 0.8 µm).

3. The noble metal catalyst of claim 1, wherein the noble metal catalyst has a total pore volume of from 0.85 to 1.5 cc/g.

4. The noble metal catalyst of claim 1, wherein the Group VIII noble metal hydrogenation component is selected from Pd, Pt, and combinations thereof.

5. The noble metal catalyst of claim 1, wherein an amount of the Group VIII noble metal hydrogenation component is in a range from 0.05 to 2.5 wt. % of the total weight of noble metal catalyst.

6. The noble metal catalyst of claim 1, wherein the support is alumina.

7. A hydro-regeneration catalyst system, comprising:
(a) a first graded bed comprising a guard bed material having 10 μm (10,000 nm) or larger pores with an average pore diameter of 100 to 1,000 μm (100,000 to 1,000,000 nm);
(b) a second graded bed, fluidly connected to the first graded bed, comprising a first noble metal catalyst comprising a first Group VIII noble metal hydrogenation component on a first support having mesopores and macropores; wherein the first noble metal catalyst has an average pore diameter of 20 to 1,000 nm (0.02 to 1 μm), a total pore volume of greater than 0.80 cc/g, and a macropore volume of 0.10 to 0.50 cc/g; and wherein the mesopores have a diameter from 10 to 20 nm and the macropores have a second diameter from 100 to 5,000 nm.

8. The hydro-regeneration catalyst system of claim 7, further comprising: (c) a third graded bed, fluidly connected and following the second graded bed, comprising a second noble metal catalyst comprising a second Group VIII noble metal hydrogenation component on a second support, the second support having mesopores; wherein the second noble metal catalyst has an average pore diameter of less than 20 nm (0.02 μm) and macropore volume less than 0.10 cc/g.

9. The hydro-regeneration catalyst system of claim 7, wherein the guard bed material is selected from one or more of carbon, silica, alumina, silica-alumina, ceramic, and resins.

10. The hydro-regeneration catalyst system of claim 7, wherein the guard bed material has an average pore diameter of 250 to 800 μm.

11. A process for hydro-regeneration of a deactivated ionic liquid catalyst containing conjunct polymer, the process comprising:
(a) contacting the deactivated ionic liquid catalyst containing the conjunct polymer with a first noble metal catalyst under first hydrogenation conditions to form a first stream comprising conjunct polymer-depleted ionic liquid catalyst, wherein the noble metal catalyst comprises a first Group VIII noble metal hydrogenation component on a first support having mesopores and macropores; wherein the first noble metal catalyst has an average pore diameter of 20 to 1,000 nm (0.02 to 1 μm), a total pore volume of greater than 0.80 cc/g, and a macropore volume of 0.10 to 0.50 cc/g; and
(b) recovering conjunct polymer-depleted ionic liquid catalyst from the first stream.

12. A process for hydro-regeneration of a deactivated ionic liquid catalyst containing conjunct polymer, the process comprising the steps of:
(a) contacting the deactivated ionic liquid catalyst containing the conjunct polymer with a first noble metal catalyst under first hydrogenation conditions to form a first stream comprising a conjunct polymer-depleted ionic liquid catalyst having a first conjunct polymer content, wherein the first noble metal catalyst comprises a first Group VIII noble metal hydrogenation component on a first support having mesopores and macropores; wherein the first noble metal catalyst has an average pore diameter of 20 to 1,000 nm (0.02 to 1 μm), a total pore volume of greater than 0.80 cc/g, and a macropore volume of 0.10 to 0.50 cc/g;
(b) contacting at least a portion of the first stream comprising conjunct polymer-depleted ionic liquid catalyst with a second noble metal catalyst under second hydrogenation conditions to form a second stream comprising a conjunct polymer-depleted ionic liquid catalyst having a second conjunct polymer content, wherein the second noble metal catalyst comprises a second Group VIII noble metal hydrogenation component on a second support having mesopores; wherein the second noble metal catalyst has an average pore diameter of less than 20 nm (0.02 μm); and
(c) recovering conjunct polymer-depleted ionic liquid catalyst from the second stream.

13. The process of claim 11 or 12, further comprising contacting the deactivated ionic liquid catalyst containing conjunct polymer with a guard bed material having 10 μm (10,000 nm) or larger pores with an average pore diameter of 100 to 1,000 μm prior to step (a).

14. The process of claim 11 or 12, further comprising recycling the recovered conjunct polymer-depleted ionic liquid catalyst to a hydrocarbon conversion process.

15. The process of claim 11 or 12, wherein the first noble metal catalyst has an average pore diameter of from 25 to 800 nm (0.025 to 0.8 μm).

16. The process of claim 11 or 12, wherein the first noble metal catalyst has a total pore volume of from 0.85 to 1.5 cc/g.

17. The process of claim 11, wherein the first support is alumina.

18. The process of claim 12, wherein the first support, the second support, or both the first support and the second support is alumina.

19. The process of claim 11 or 12, wherein the deactivated ionic liquid catalyst is a chloroaluminate ionic liquid catalyst.

* * * * *